US011986549B2

(12) United States Patent
Liard et al.

(10) Patent No.: US 11,986,549 B2
(45) Date of Patent: May 21, 2024

(54) METHOD FOR TREATING KERATIN FIBERS USING A COMPOSITION COMPRISING AT LEAST ONE SILICONE ACRYLIC COPOLYMER AND AT LEAST ONE PIGMENT

(71) Applicant: L'OREAL, Paris (FR)

(72) Inventors: Alexis Liard, Saint-Ouen (FR); Karine Lucet-Levannier, Saint-Ouen (FR)

(73) Assignee: L'OREAL, Paris (FR)

( * ) Notice: Subject to any disclaimer, the term of this patent is extended or adjusted under 35 U.S.C. 154(b) by 354 days.

(21) Appl. No.: 17/287,799

(22) PCT Filed: Oct. 18, 2019

(86) PCT No.: PCT/EP2019/078448
§ 371 (c)(1),
(2) Date: Apr. 22, 2021

(87) PCT Pub. No.: WO2020/083789
PCT Pub. Date: Apr. 30, 2020

(65) Prior Publication Data
US 2021/0393505 A1    Dec. 23, 2021

(30) Foreign Application Priority Data

Oct. 25, 2018  (FR) ...................................... 1859875

(51) Int. Cl.
| | | |
|---|---|---|
| *A61Q 5/00* | (2006.01) | |
| *A61K 8/893* | (2006.01) | |
| *A61Q 1/14* | (2006.01) | |
| *A61Q 5/06* | (2006.01) | |

(52) U.S. Cl.
CPC ................ *A61K 8/893* (2013.01); *A61Q 1/14* (2013.01); *A61Q 5/06* (2013.01); *A61K 2800/43* (2013.01); *A61K 2800/884* (2013.01)

(58) Field of Classification Search
CPC ................ A61K 8/893; A61K 2800/43; A61K 2800/884; A61K 8/37; A61K 8/39; A61Q 1/14; A61Q 5/06
USPC .......................................................... 8/405
See application file for complete search history.

(56) References Cited

U.S. PATENT DOCUMENTS

| | | | |
|---|---|---|---|
| 4,578,266 A | 3/1986 | Tietjen et al. | |
| 4,957,732 A | 9/1990 | Grollier et al. | |
| 5,061,481 A | 10/1991 | Suzuki et al. | |
| 5,219,560 A | 6/1993 | Suzuki et al. | |
| 5,645,609 A | 7/1997 | Andrean et al. | |
| 5,990,479 A | 11/1999 | Weiss et al. | |
| 6,106,577 A | 8/2000 | Audousset et al. | |
| 6,225,198 B1 | 5/2001 | Alivisatos et al. | |
| 6,716,455 B2 | 4/2004 | Birkel et al. | |
| 7,942,937 B2 | 5/2011 | Brun | |
| 10,105,308 B2 | 10/2018 | Goutsis et al. | |
| 2005/0186165 A1 | 8/2005 | Mathonneau et al. | |
| 2006/0085924 A1 | 4/2006 | Brun | |
| 2006/0088493 A1 | 4/2006 | Vic et al. | |
| 2008/0269352 A1 | 10/2008 | Falkowski et al. | |
| 2009/0151086 A1* | 6/2009 | Brun .................... | A61K 8/8152 8/405 |
| 2010/0183536 A1 | 7/2010 | Ansmann et al. | |
| 2015/0174051 A1* | 6/2015 | Teboul ..................... | A61K 8/25 424/70.6 |
| 2015/0320664 A1 | 11/2015 | Bebot et al. | |
| 2016/0030307 A1 | 2/2016 | Chen et al. | |
| 2016/0235658 A1 | 8/2016 | Herrlein et al. | |

FOREIGN PATENT DOCUMENTS

| | | | | |
|---|---|---|---|---|
| DE | 102014221535 A1 | 4/2016 | | |
| EP | 0186507 A2 | 7/1986 | | |
| EP | 0342834 A2 | 11/1989 | | |
| EP | 1184426 A2 | 3/2002 | | |
| EP | 1287810 A1 | 3/2003 | | |
| EP | 1649898 A2 | 4/2006 | | |
| EP | 2070516 A1 | 6/2009 | | |
| FR | 2679771 A1 | 2/1993 | | |
| FR | 2741530 A1 | 5/1997 | | |
| FR | 2970177 A1 * | 7/2012 | ............... | A61K 8/37 |
| JP | 05-017710 A | 1/1993 | | |
| JP | 07-258460 A | 10/1995 | | |
| JP | 09-188830 A | 7/1997 | | |
| JP | 10-158450 A | 6/1998 | | |
| JP | 10-158451 A | 6/1998 | | |
| JP | 5745266 B2 | 7/2015 | | |
| WO | 97/01321 A1 | 1/1997 | | |
| WO | 2007068371 A1 | 6/2007 | | |

(Continued)

OTHER PUBLICATIONS

International Search Report and Written Opinion for counterpart Application No. PCT/EP2019/078446, dated Jan. 2, 2020.
International Search Report and Written Opinion for counterpart Application No. PCT/EP2019/078448, dated Jan. 2, 2020.
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.
GOO Chemical: "Personal Care Product Catalogue for Cosmetics," Internet Citation, Jan. 2015, pp. 1-12, XP002759716, Retrieved from the Internet: http://www.goo-chem.co.jp/english/product/pdf/cosmetic/cosmetics_catalogue_en_2013.pdf [retrieved on Jul. 11, 2016].
Hansen, C.M., "The Three Dimensional Solubility Parameters," J. Paint Technol. 39, 105 (1967).

(Continued)

*Primary Examiner* — Eisa B Elhilo
(74) *Attorney, Agent, or Firm* — The Marbury Law Group PLLC

(57) ABSTRACT

A method for treating human keratin fibers such as the hair is described and comprises the application to the keratin fibers of a dye composition comprising at least one silicone acrylic copolymer and at least one pigment, optionally the application of heat to the dyed keratin fibers using a heating tool and the application to the dyed keratin fibers of a makeup-removing composition comprising at least one hydrocarbon oil.

19 Claims, No Drawings

(56) References Cited

FOREIGN PATENT DOCUMENTS

| WO | 2008/155059 A2 | 12/2008 |
| WO | 2012/095410 A1 | 7/2012 |
| WO | 2017/109146 A1 | 6/2017 |
| WO | 2020/083787 A1 | 4/2020 |

OTHER PUBLICATIONS

Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, 1997, pp. 7019-7029.

Schlossman, Mitchell L., "Treated Pigments New Ways to Impart Color on the Skin," Cosmetics and Toiletries, vol. 105, Feb. 1990, pp. 53-64.

Grulke, "Solubility Parameter Values," Polymer Handbook, 3rd Edition, Chapter VII, pp. 519-559.

Non-Final Office Action for copending U.S. Appl. No. 17/287,770, dated Apr. 20, 2022.

STIC Search Report dated Nov. 2, 2021.

* cited by examiner

METHOD FOR TREATING KERATIN FIBERS USING A COMPOSITION COMPRISING AT LEAST ONE SILICONE ACRYLIC COPOLYMER AND AT LEAST ONE PIGMENT

CROSS REFERENCE TO RELATED APPLICATION

This is a national stage application of PCT/EP2019/078448, filed internationally on Oct. 18, 2019, which claims priority to French Application No. 1859875, filed on Oct. 25, 2018, both of which are incorporated by reference herein in their entireties.

The subject of the present invention is a method for treating keratin fibers such as the hair, comprising the application to the keratin fibers of a dye composition comprising at least one silicone acrylic copolymer and at least one pigment, and the application to the dyed keratin fibers of a makeup-removing composition comprising at least one hydrocarbon oil.

In the field of dyeing keratin fibers, in particular human keratin fibers, it is already known practice to dye keratin fibers via various techniques using direct dyes or pigments for non-permanent dyeing, or dye precursors for permanent dyeing.

There are essentially three types of process for dyeing the hair:

a) "permanent" dyeing, the function of which is to afford a substantial modification to the natural color and which uses oxidation dyes which penetrate into the hair fiber and forms the dye via an oxidative condensation process;

b) non-permanent, semi-permanent or direct dyeing, which does not use the oxidative condensation process and withstands four or five shampoo washes; it consists in dyeing keratin fibers with dye compositions containing direct dyes. These dyes are colored and coloring molecules that have affinity for keratin fibers;

c) temporary dyeing, which gives rise to a modification of the natural color of the head of hair that remains from one shampoo wash to the next, and which serves to enhance or correct a shade that has already been obtained. It may also be likened to a "makeup" process.

For this last type of dyeing, it is known practice to use colored polymers formed by grafting one or more dyes of azo, triphenylmethane, azine, indoamine or anthraquinone nature onto a polymer chain. These colored polymers are not entirely satisfactory, especially as regards the homogeneity of the coloring obtained and its resistance, not to mention the problems associated with their manufacture and especially with their reproducibility.

Another dyeing method consists in using pigments. Specifically, the use of pigment on the surface of keratin fibers generally makes it possible to obtain visible colorings on dark hair, since the surface pigment masks the natural color of the fiber. The use of pigment for dyeing keratin fibers is described, for example, in patent application FR 2741530, which recommends using, for the temporary dyeing of keratin fibers, a composition comprising at least one dispersion of film-forming polymer particles comprising at least one acid function and at least one pigment dispersed in the continuous phase of said dispersion. The colorings obtained via this dyeing method have the drawback of having a low resistance to shampoo washes.

It is moreover known practice to color coat the hair using a composition comprising an electrophilic monomer of cyanoacrylate type, and a pigment, in particular in document EP 1649898. Such a composition makes it possible to obtain completely coated and non-greasy hair. However, the coating obtained is not entirely satisfactory in the face of external agents such as washing and perspiration. Moreover, the coating obtained is sensitive to fatty substances such as sebum.

In addition, compositions for temporarily dyeing the hair may also lead to a hair feel that is uncosmetic and/or not natural; the hair thus dyed may in particular lack softness and/or suppleness and/or strand separation.

Moreover, these temporary hair dye compositions may also have the drawback of transferring, i.e. of becoming at least partly deposited, leaving marks, on certain supports with which they may be placed in contact and in particular clothing or the skin.

In addition, there are no effective makeup-removing compositions for removing this type of temporary dye composition when it is resistant to shampoo washes.

Therefore there remains a need for a method for treating keratin fibers, in particular hair, which has the advantage of obtaining a homogeneous and smooth colored coating on the hair, and also hair with complete strand separation, while forming a coating that is resistant to shampoo washes and to the various attacking factors to which hair may be subjected without degradation of the keratin fibers, which does not transfer and which is easily removed.

Thus, the objective of the present invention is to develop a method for treating keratin fibers which has the advantage of obtaining a homogeneous and smooth colored coating on the hair, and also hair with complete strand separation, while forming a coating that is resistant to shampoo washes and to the various attacking factors to which hair may be subjected without degradation of the keratin fibers, which does not transfer and which is easily removed.

This objective is achieved with the present invention, the subject of which is a method for treating human keratin fibers such as the hair, comprising the following steps:

a) applying to the keratin fibers a dye composition comprising:
  at least one silicone acrylic copolymer, and
  at least one pigment, and b) optionally applying heat to the dyed keratin fibers using a heating tool, and c) applying to the dyed keratin fibers a makeup-removing composition comprising at least one hydrocarbon oil.

Through the use of this method, colored coatings are obtained on the keratin fibers that make it possible to obtain a coloring that is visible on all types of hair in a shampoo-resistant manner while preserving the physical qualities of the keratin fibers. Such a coating may be resistant to the external attacking factors to which the hair may be subjected, such as blow-drying and perspiration. This method makes it possible to obtain hair with complete strand separation, that can be styled without problems, and from which the makeup can be removed easily either immediately after the application of the dye composition once the step of heating has been applied to the hair when the method involves a heat application step, or after a certain time, i.e. a few days to a few weeks, after the application of the dye composition and optionally after the step of heating has been applied to the hair.

The term "hair with strand separation" means hair which, after application of the composition and drying, is not stuck together (or of which all the strands are separated from each other) and thus does not form clumps of hair.

For the purposes of the present invention, the term "shampoo-resistant coloring" means that the coloring obtained remains after one shampoo wash, preferably after 3 shampoo washes, more preferentially after 5 shampoo washes, more preferentially still after 10 shampoo washes.

The invention is not limited to the examples illustrated. The features of the various examples may notably be combined within variants which are not illustrated.

The expression "comprising a" should be understood as meaning "comprising at least one", unless specified to the contrary.

The expression "at least one" means "one or more".

The treatment method is preferably a cosmetic treatment method comprising a step of dyeing keratin fibers such as the hair followed by a step of removing makeup from and/or cleansing keratin fibers such as the hair.

The method according to the invention comprises a step of applying a dye composition to keratin fibers such as the hair.

Dye Composition

The dye composition according to the invention is preferably a cosmetic composition for dyeing keratin fibers, in particular human keratin fibers such as the hair.

Silicone Acrylic Copolymer

The dye composition according to the method according to the invention comprises at least one silicone acrylic copolymer.

Preferably, the copolymer according to the invention is water insoluble. For the purposes of the present invention, the term "water insoluble" means a compound that is insoluble in water at ordinary temperature (25° C.) and at atmospheric pressure (760 mmHg or $1.013 \times 10^5$ Pa). Preferably, the copolymer according to the invention has a solubility in water of less than 5%, better still less than 1% and more preferentially still less than 0.1%.

Preferably, the dye composition comprises at least one silicone acrylic copolymer, comprising at least the following units:
  a) a polyalkylsiloxane unit, and
  b) an alkyl acrylate or methacrylate unit, preferably at least two alkyl acrylate or methacrylate units, the alkyl radical comprising from 1 to 30 carbon atoms, preferentially from 1 to 22 carbon atoms, better still 1 to 10 carbon atoms, and more preferentially 2 to 6 carbon atoms.

An "alkyl acrylate or methacrylate unit" means a unit derived from an alkyl acrylate or methacrylate monomer.

Preferentially, the dye composition comprises at least one silicone acrylic copolymer, comprising at least the following units:
  a) a polydimethylsiloxane (PDMSs) unit, and
  b) an alkyl acrylate or methacrylate unit, preferably at least two alkyl acrylate or methacrylate units, the alkyl radical comprising from 1 to 30 carbon atoms, preferentially from 1 to 22 carbon atoms, better still 1 to 10 carbon atoms, and more preferentially 2 to 6 carbon atoms.

The term "polydimethylsiloxanes" (also abbreviated as PDMSs) denotes, in accordance with what is generally accepted, any organosilicon polymer or oligomer of linear structure, of variable molecular weight, obtained by polymerization and/or polycondensation of suitably functionalized silanes, and constituted essentially of a repetition of main units in which the silicon atoms are linked together via oxygen atoms (siloxane bond ° Si—O—Si═), comprising methyl radicals directly linked via a carbon atom to said silicon atoms.

The PDMS chains which can be used to obtain the copolymer used according to the invention comprise at least one polymerizable radical group, preferably located on at least one of the ends of the chain, that is to say that the PDMS can, for example, have a polymerizable radical group on each of the two ends of the chain or have a polymerizable radical group on one end of the chain and a trimethylsilyl end group on the other end of the chain.

A polymerizable radical group is understood to mean a radical capable of polymerizing with other polymerizable radical groups or monomers.

Preferably, the polydimethylsiloxane unit comprises at least one polymerizable radical group.

Preferably, the polydimethylsiloxane unit comprises at least two polymerizable radical groups, more preferentially at least one polymerizable radical group on each of the two ends of the chain.

Preferably, the polymerizable radical group is an acrylic or methacrylic group having from 1 to 6 carbon atoms, more preferentially a $CH_2$=CH—CO—O—$R_1$— group, where $R_1$ represents an alkyl radical comprising from 1 to 3 carbon atoms.

The copolymers used in the dye composition are generally obtained according to the usual methods of polymerization and grafting, for example by radical polymerization (A) of a polyalkylsiloxane comprising at least one polymerizable radical group (for example on one of the ends of the chain or on both ends) and (B) of at least one acrylic or methacrylic monomer, such as acrylic acid, methacrylic acid or an ester thereof, as described, for example, in the documents U.S. Pat. Nos. 5,061,481 and 5,219,560.

More particularly, the silicone acrylic copolymer comprises at least the following units:
  a) a polydimethylsiloxane (PDMS) unit comprising at least one polymerizable radical group chosen from an acrylic or methacrylic group having from 1 to 6 carbon atoms, more preferentially a $CH_2$=CH—CO—O—$R_1$— group, where $R_1$ represents an alkyl radical comprising from 1 to 3 carbon atoms; and
  b) a $C_1$-$C_{30}$, preferably $C_1$-$C_{22}$, preferentially $C_1$-$C_{10}$ and better still $C_2$-$C_6$ alkyl acrylate or methacrylate unit.

Even more particularly, the dye composition of use in the method according to the invention comprises at least one silicone acrylic copolymer comprising at least the following units:
  a) a polydimethylsiloxane (PDMS) unit comprising at least one polymerizable radical group chosen from a $CH_2$=CH—CO—O—$R_1$— group, where $R_1$ represents an alkyl radical comprising from 1 to 3 carbon atoms; and
  b) a $C_1$-$C_{22}$, preferably $C_1$-$C_{10}$ and better still $C_2$-$C_6$ alkyl acrylate or methacrylate unit.

Even more particularly, the dye composition of use in the method according to the invention comprises at least one silicone acrylic copolymer comprising at least the following units:
  a) a polydimethylsiloxane (PDMS) unit comprising at least two polymerizable radical groups chosen from a $CH_2$=CH—CO—O—$R_1$— group, where $R_1$ represents an alkyl radical comprising from 1 to 3 carbon atoms, more preferentially at least one polymerizable radical group on each of the two ends of the chain; and
  b) a $C_1$-$C_{22}$, preferably $C_1$-$C_{10}$ and better still $C_2$-$C_6$ alkyl acrylate or methacrylate unit.

More particularly still, the silicone acrylic copolymer according to the invention is a copolymer with the INCI name isobutyl methacrylate/bis-hydroxypropyl dimethicone acrylate copolymer, such as for example the compound sold by Grant Industries under the name Granacrysil BMAS.

It is an isobutyl methacrylate/bis-hydroxypropyl dimethicone acrylate copolymer in solution in isododecane.

The silicone acrylic copolymer(s) may be present in a total amount ranging from 1% to 50% by weight, preferably from 2% to 40% by weight, more preferentially from 3% to 30% by weight and better still from 5% to 20% by weight relative to the total weight of the dye composition.

Pigments

The dye composition comprises one or more pigments.

The term "pigment" means white or colored particles of any shape, which are insoluble in the composition in which they are present.

The pigments that may be used are especially chosen from the organic and/or mineral pigments known in the art, notably those described in Kirk-Othmer's Encyclopedia of Chemical Technology and in Ullmann's Encyclopedia of Industrial Chemistry.

They may be natural, of natural origin, or non-natural.

These pigments may be in pigment powder or paste form. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" means any pigment that satisfies the definition in Ullmann's encyclopedia in the chapter on inorganic pigments. Among the mineral pigments that are useful in the present invention, mention may be made of ochres such as red ochre (clay (in particular kaolinite) and iron hydroxide (for example hematite)), brown ochre (clay (in particular kaolinite) and limonite), yellow ochre (clay (in particular kaolinite) and goethite); titanium dioxide, optionally surface treated; zirconium oxide or cerium oxide; zinc oxide, iron oxide (black, yellow or red) or chromium oxide; manganese violet, ultramarine blue, chromium hydrate and ferric blue; metal powders such as aluminum powder or copper powder.

Mention may also be made of alkaline-earth metal carbonates (such as calcium carbonate or magnesium carbonate), silicon dioxide, quartz and any other compound used as inert filler in cosmetic compositions, provided that these compounds contribute color or whiteness to the composition under the conditions under which they are employed.

The pigment may be an organic pigment. The term "organic pigment" means any pigment that satisfies the definition in Ullmann's encyclopedia in the chapter on organic pigments.

The organic pigment may especially be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

Use may also be made of any mineral or organic compound that is insoluble in the composition and standard in the cosmetics field, provided that these compounds contribute color or whiteness to the composition under the conditions under which they are employed, for example guanine, which, according to the refractive index of the composition, is a pigment.

In particular, the white or colored organic pigments may be chosen from carmine, carbon black, aniline black, azo yellow, quinacridone, phthalocyanine blue, the blue pigments codified in the Color Index under the references CI 42090, 69800, 69825, 73000, 74100, 74160, the yellow pigments codified in the Color Index under the references CI 11680, 11710, 15985, 19140, 20040, 21100, 21108, 47000, 47005, the green pigments codified in the Color Index under the references CI 61565, 61570, 74260, the orange pigments codified in the Color Index under the references CI 11725, 15510, 45370, 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenol derivatives as described in patent FR 2679771.

Examples that may also be mentioned include pigment pastes of organic pigment, such as the products sold by the company Hoechst under the names:

Cosmenyl Yellow IOG: Yellow 3 pigment (CI 11710);
Cosmenyl Yellow G: Yellow 1 pigment (CI 11680);
Cosmenyl Orange GR: Orange 43 pigment (CI 71105);
Cosmenyl Red R: Red 4 pigment (CI 12085);
Carmine Cosmenyl FB: Red 5 pigment (CI 12490);
Cosmenyl Violet RL: Violet 23 pigment (CI 51319);
Cosmenyl Blue A2R: Blue 15.1 pigment (CI 74160);
Cosmenyl Green GG: Green 7 pigment (CI 74260);
Cosmenyl Black R: Black 7 pigment (CI 77266).

The pigments in accordance with the invention may also be in the form of composite pigments, as described in patent EP 1184426. These composite pigments may be composed notably of particles comprising a mineral core, at least one binder, for attaching the organic pigments to the core, and at least one organic pigment which at least partially covers the core.

The organic pigment may also be a lake. The term "lake" means dyes adsorbed onto insoluble particles, the assembly thus obtained remaining insoluble during use.

The mineral substrates onto which the dyes are adsorbed are, for example, alumina, silica, calcium sodium borosilicate or calcium aluminum borosilicate and aluminum.

Among the dyes, mention may be made of carminic acid. Mention may also be made of the dyes known under the following names: D&C Red 21 (CI 45380), D&C Orange 5 (CI 45370), D&C Red 27 (CI 45410), D&C Orange 10 (CI 45425), D&C Red 3 (CI 45430), D&C Red 4 (CI 15510), D&C Red 33 (CI 17200), D&C Yellow 5 (CI 19 140), D&C Yellow 6 (CI 15985), D&C Green (CI 61570), D&C Yellow 10 (CI 47005), D&C Green 3 (CI 42053), D&C Blue 1 (CI 42090).

An example of a lake that may be mentioned is the product known under the following name: D&C Red 7 (CI 15850:1).

The pigment may also be a pigment with special effects. The term "pigments with special effects" means pigments that generally create a colored appearance (characterized by a certain shade, a certain vivacity and a certain level of luminance) that is non-uniform and that changes as a function of the conditions of observation (light, temperature, angles of observation, etc.). They thereby contrast with colored pigments, which afford a conventional opaque, semitransparent or transparent, uniform color.

Several types of pigment with special effects exist: those with a low refractive index, such as fluorescent or photochromic pigments, and those with a higher refractive index, such as nacres, interference pigments or glitter flakes.

Examples of pigments with special effects that may be mentioned include nacreous pigments such as mica coated with titanium or with bismuth oxychloride, colored nacreous pigments such as mica coated with titanium and iron oxides, mica coated with iron oxide, mica coated with titanium and especially with ferric blue or with chromium oxide, mica coated with titanium and with an organic pigment as defined above, and also nacreous pigments based on bismuth oxychloride. Nacreous pigments that may be mentioned include the Cellini nacres sold by Engelhard (mica-$TiO_2$-lake), Prestige sold by Eckart (mica-$TiO_2$), Prestige Bronze sold by Eckart (mica-$Fe_2O_3$), and Colorona sold by Merck (mica-$TiO_2$—$Fe_2O_3$).

Mention may also be made of the gold-colored nacres sold especially by Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by Merck under the name Bronze fine (17384) (Colorona) and Bronze (17353) (Colorona) and by Engelhard under the name Super bronze (Cloisonne); the orange nacres sold especially by Engelhard under the name Orange 363C (Cloisonne) and Orange MCR 101 (Cosmica) and by Merck under the name Passion orange (Colorona) and Matte orange (17449) (Microna); the brown-colored nacres sold especially by Engelhard under the name Nu-antique copper 340XB (Cloisonne) and Brown CL4509 (Chromalite); the nacres with a coppery glint sold especially by Engelhard under the name Copper 340A (Timica); the nacres with a red glint sold especially by Merck under the name Sienna fine (17386) (Colorona); the nacres with a yellow glint sold especially by Engelhard under the name Yellow (4502) (Chromalite); the red-colored nacres with a gold glint sold especially by Engelhard under the name Sunstone G012 (Gemtone); the pink nacres sold especially by Engelhard under the name Tan opale G005 (Gemtone); the black nacres with a gold glint sold especially by Engelhard under the name Nu antique bronze 240 AB (Timica), the blue nacres sold especially by Merck under the name Matte blue (17433) (Microna), the white nacres with a silvery glint sold especially by Merck under the name Xirona Silver, and the golden-green pink-orange nacres sold especially by Merck under the name Indian summer (Xirona), and mixtures thereof.

Still as examples of nacres, mention may also be made of particles comprising a borosilicate substrate coated with titanium oxide.

Particles comprising a glass substrate coated with titanium oxide are sold in particular under the name Metashine MC1080RY by the company Toyal.

Finally, as examples of nacres, mention may also be made of polyethylene terephthalate glitter flakes, especially those sold by the company Meadowbrook Inventions under the name Silver 1P 0.004×0.004 (silver glitter flakes).

It is also possible to envisage multilayer pigments based on synthetic substrates, such as alumina, silica, calcium sodium borosilicate or calcium aluminum borosilicate and aluminum.

The pigments with special effects may also be chosen from reflective particles, i.e. especially from particles whose size, structure, especially the thickness of the layer(s) of which they are made and their physical and chemical natures, and surface finish, allow them to reflect incident light. This reflection may, where appropriate, have an intensity sufficient to create at the surface of the composition or of the mixture, when it is applied to the support to be made up, highlight points that are visible to the naked eye, i.e. more luminous points that contrast with their environment by appearing to sparkle.

The reflective particles may be selected so as not to significantly alter the coloring effect generated by the coloring agents with which they are combined, and more particularly so as to optimize this effect in terms of color rendition. They may more particularly have a yellow, pink, red, bronze, orange, brown, gold and/or coppery color or glint.

These particles may have varied forms and may especially be in platelet or globular form, in particular in spherical form.

Irrespective of their form, the reflective particles may or may not have a multilayer structure, and, in the case of a multilayer structure, may have, for example, at least one layer of uniform thickness, especially of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles including a mineral substrate coated with a layer of metal, mention may also be made of particles including a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the names Crystal Star GF 550 and GF 2525 by this same company.

Use may also be made of particles comprising a metal substrate, such as silver, aluminum, iron, chromium, nickel, molybdenum, gold, copper, zinc, tin, magnesium, steel, bronze or titanium, said substrate being coated with at least one layer of at least one metal oxide, such as titanium oxide, aluminum oxide, iron oxide, cerium oxide, chromium oxide, silicon oxides and mixtures thereof.

Examples that may be mentioned include aluminum powder, bronze powder or copper powder coated with $SiO_2$ sold under the name Visionaire by Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductor nanoparticles that are capable of emitting, under light excitation, radiation with a wavelength of between 400 nm and 700 nm. These nanoparticles are known from the literature. In particular, they may be synthesized according to the processes described, for example, in U.S. Pat. No. 6,225,198 or 5,990,479, in the publications cited therein and also in the following publications: Dabboussi B. O. et al., "(CdSe)ZnS core-shell quantum dots: synthesis and characterisation of a size series of highly luminescent nanocrystallites", Journal of Physical Chemistry B, vol. 101, 1997, pages 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pages 7019-7029.

The variety of pigments that may be used in the present invention makes it possible to obtain a wide range of colors, and also particular optical effects such as metallic effects or interference effects.

The size of the pigment used in the dye composition according to the present invention is generally between 10 nm and 200 µm, preferably between 20 nm and 80 µm and more preferably between 30 nm and 50 µm.

The pigments may be dispersed in the product by means of a dispersant.

The dispersant serves to protect the dispersed particles against agglomeration or flocculation thereof. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters in particular and $C_8$ to $C_{20}$ fatty acid esters of polyols such as glycerol or diglycerol are used, such as poly(12-hydroxystearic acid) stearate with a molecular weight of approximately 750 g/mol, such as the product sold under the name Solsperse 21000 by Avecia, polyglyceryl-2 dipolyhydroxystearate (CTFA name) sold under the reference Dehymyls PGPH by Henkel, or else polyhydroxystearic acid such as the product sold under the reference Arlacel P100 by Uniqema, and mixtures thereof.

As other dispersants that may be used in the compositions of the invention, mention may be made of quaternary ammonium derivatives of polycondensed fatty acids, for instance Solsperse 17000 sold by Avecia, and polydimethylsiloxane/oxypropylene mixtures such as those sold by Dow Corning under the references DC2-5185 and DC2-5225 C.

The pigments used in the dye composition according to the invention may be surface treated with an organic agent.

Thus, the pigments that have been surface treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminum salts of fatty acids, for example aluminum stearate or laurate; metal alkoxides; polyethylene; (meth) acrylic polymers, for example polymethyl methacrylates; polymers and copolymers containing acrylate units; alkanolamines; silicone compounds, for example silicones, in particular polydimethylsiloxanes; organofluorine compounds, for example perfluoroalkyl ethers; fluorosilicone compounds.

The surface-treated pigments that are useful in the dye composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available as is.

Preferably, the surface-treated pigments are coated with an organic layer.

Preferably, the dye composition according to the invention comprises at least one pigment surface treated with an organic agent chosen from silicone compounds such as silicones, in particular polydimethylsiloxanes.

The organic agent with which the pigments are treated may be deposited on the pigments by solvent evaporation, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is notably described in patent U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 20% by weight of the total weight of the surface-treated pigment.

Preferably, the surface treatments of the pigments are chosen from the following treatments:

- a PEG-silicone treatment, for instance the AQ surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- a magnesium myristate treatment, for instance the MM surface treatment sold by LCW;
- an aluminum dimyristate treatment, such as the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrosiloxane/perfluoroalkyl phosphate treatment, for instance the FS01 surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- an acrylate copolymer treatment, for instance the APD surface treatment sold by Daito;

a perfluoroalkyl phosphate/isopropyl titanium triisostearate treatment, for instance the PF+ITT surface treatment sold by Daito.

According to one particular embodiment of the invention, the dispersant is present with organic or mineral pigments in submicron-sized particulate form in the dye composition.

The term "submicron" is understood to mean pigments having a particulate size that has been micronized by a micronization method and having a mean particle size of less than a micrometer (µm), in particular between 0.1 and 0.9 µm, and preferably between 0.2 and 0.6 µm.

According to one embodiment, the dispersant and the pigment or pigments are present in an amount (dispersant: pigment) of between 0.5:1 and 2:1, particularly between 0.75:1 and 1.5:1 or better still between 0.8:1 and 1.2:1.

According to one particular embodiment, the dispersant is suitable for dispersing the pigments and is compatible with a condensation-curable formulation.

The term "compatible" is understood to mean, for example, that said dispersant is miscible in the oily phase of the composition or of the dispersion containing the pigment(s), and it does not retard or reduce the curing. The dispersant is preferably cationic.

The dispersant(s) may therefore have a silicone backbone, such as silicone polyether and dispersants of aminosilicone type. Among the suitable dispersants, mention may be made of:
  aminosilicones, i.e. silicones comprising one or more amino groups such as those sold under the names and references: BYK LPX 21879 by BYK, GP-4, GP-6, GP-344, GP-851, GP-965, GP-967 and GP-988-1, sold by Genesee Polymers,
  silicone acrylates such as Tego® RC 902, Tego® RC 922, Tego® RC 1041, and Tego® RC 1043, sold by Evonik,
  polydimethylsiloxane (PDMS) silicones with carboxyl groups such as X-22162 and X-22370 by Shin-Etsu, epoxy silicones such as GP-29, GP-32, GP-502, GP-504, GP-514, GP-607, GP-682, and GP-695 by Genesee Polymers, or Tego® RC 1401, Tego® RC 1403, Tego® RC 1412 by Evonik.

According to one particular embodiment, the dispersant(s) is (are) of aminosilicone type and are positively charged.

Preferably, the pigment(s) is (are) chosen from mineral, mixed mineral-organic or organic pigments.

Preferably, the dye composition according to the invention comprises at least one organic pigment surface treated with an organic agent chosen from silicone compounds such as silicones, in particular polydimethylsiloxanes.

The total amount of pigment(s) may range from 0.01% to 30% by weight, more particularly from 0.05% to 20% by weight, preferably from 0.1% to 15% by weight and preferably from 1% to 10% by weight relative to the total weight of the dye composition.

The dye composition of the invention may contain other colored or coloring species different from the pigments according to the invention, such as direct dyes or oxidation dye precursors.

The dye composition according to the invention may comprise water, which is preferably present in a content ranging from 0.1% to 50% by weight, more preferentially from 0.5% to 30% by weight, relative to the weight of the composition.

The dye composition according to the invention may comprise less than 2% by weight of water or even less than 0.5% by weight of water, relative to the total weight of the dye composition.

Preferably, the dye composition does not comprise any water.

Oils

The dye composition may comprise one or more oils.

Preferably, the dye composition may comprise one or more oils chosen from alkanes.

The term "oil" means a fatty substance that is liquid at room temperature (25° C.) and at atmospheric pressure (760 mmHg or $1.013 \times 10^5$ Pa).

The oil can be volatile or non-volatile.

The term "volatile oil" means an oil that can evaporate on contact with the skin in less than one hour, at room temperature and atmospheric pressure. The volatile oil is a cosmetic volatile oil, which is liquid at room temperature. More specifically, a volatile oil has an evaporation rate of between 0.01 and 200 mg/cm²/min, limits included (see protocol for measuring the evaporation rate indicated in the text below).

The term "non-volatile oil" means an oil that remains on the skin or the keratin fiber at room temperature and atmospheric pressure. More specifically, a non-volatile oil has an evaporation rate of strictly less than 0.01 mg/cm²/min (see protocol for measuring the evaporation rate indicated in the text below).

Preferably, the dye composition comprises one or more oils chosen from $C_6$-$C_{16}$ alkanes and/or mixtures thereof.

As regards the $C_6$-$C_{16}$ alkanes, they may be linear or branched, and possibly cyclic.

Mention may in particular be made of branched $C_8$-$C_{16}$ alkanes, such as $C_6$-$C_{16}$ isoalkanes (also known as isoparaffins), isododecane, isodecane or isohexadecane, and for example the oils sold under the Isopar or Permethyl trade names, and mixtures thereof. Mention may also be made of linear alkanes, preferably of plant origin, comprising from 7 to 15 carbon atoms, in particular from 9 to 14 carbon atoms and more particularly from 11 to 13 carbon atoms.

As examples of linear alkanes that are suitable for the invention, mention may be made of n-heptane (C7), n-octane (C8), n-nonane (C9), n-decane (C10), n-undecane (C11), n-dodecane (C12), n-tridecane (C13), n-tetradecane (C14) and n-pentadecane (C15), and mixtures thereof, and in particular the mixture of n-undecane (C11) and n-tridecane (C13) described in Example 1 of patent application WO 2008/155059 by the company Cognis.

Mention may also be made of n-dodecane (C12) and n-tetradecane (C14) sold by Sasol under the references, respectively, Parafol 12-97 and Parafol 14-97, and also mixtures thereof.

As examples of alkanes that are suitable for the invention, mention may be made of the alkanes described in patent applications WO 2007/068371 and WO 2008/155059. These alkanes are obtained from fatty alcohols, which are themselves obtained from coconut oil or palm oil.

According to a particular embodiment, the dye composition comprises isododecane. Such a compound is, for example, the isododecane sold under the reference Isododecane by Ineos.

Preferably, the dye composition according to the invention comprises one or more oils selected from $C_8$-$C_{16}$ alkanes, more preferentially from isododecane, isohexadecane, tetradecane and/or mixtures thereof.

Preferably, the dye composition comprises isododecane.

The dye composition according to the invention may comprise one or more oils present in a total amount of between 10% and 99% by weight, preferably between 20% and 95% by weight and better still between 30% and 90% by weight, relative to the total weight of the dye composition.

Organic Solvents

The dye composition according to the invention may comprise one or more organic solvents different from the oils described above, in particular different from alkanes.

Examples of organic solvents that may be mentioned include lower $C_1$-$C_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

When they are present, the organic solvents are present in a total amount preferably inclusively between 0.10% and 20% by weight approximately relative to the total weight of the dye composition and more preferentially between 1% and 15% by weight and even more particularly inclusively between 5% and 10% by weight relative to the total weight of the dye composition.

Additives

The dye composition according to the invention may also contain at least one agent customarily used in cosmetics, for example chosen from reducing agents, thickeners, softeners, antifoams, moisturizers, UV-screening agents, peptizers, solubilizers, fragrances, anionic, cationic, nonionic or amphoteric surfactants, proteins, vitamins, cationic polymers, silicone polymers other than the silicon acrylic polymers described above.

The dye composition according to the invention may comprise one or more silicones, which may be solid or liquid, and volatile or non-volatile.

The silicones that may be used may be soluble or insoluble in the dye composition according to the invention; they may be in the form of oil, wax, resin or gum; silicone oils and gums are preferred.

Silicones are especially described in detail in Walter Noll's Chemistry and Technology of Silicones (1968), Academic Press.

The volatile silicones may be chosen from those with a boiling point of between 60° C. and 260° C. (at atmospheric pressure) and more particularly from:

i) cyclic polydialkylsiloxanes comprising from 3 to 7 and preferably 4 to 5 silicon atoms, such as
octamethylcyclotetrasiloxane and decamethylcyclopentasiloxane.

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia;
cyclocopolymers of the dimethylsiloxane/methylalkylsiloxane type having the chemical structure:

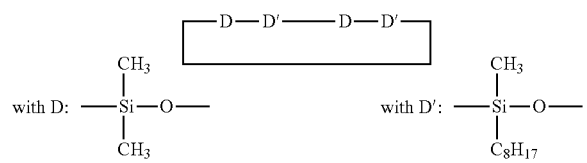

Mention may be made of Volatile Silicone FZ 3109 sold by the company Union Carbide;
mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear polydialkylsiloxanes containing 2 to 9 silicon atoms, which generally have a viscosity of less than or equal to $5 \times 10^{-6}$ m$^2$/s at 25° C., such as decamethyltetrasiloxane.

Other silicones belonging to this category are described in the article published in Cosmetics and Toiletries, Vol. 91, January 76, pages 27-32, Todd & Byers "Volatile Silicone Fluids for Cosmetics"; mention may be made of the product sold under the name SH 200 by the company Toray Silicone.

Among the non-volatile silicones, mention may be made, alone or as a mixture, of polydialkylsiloxanes and especially polydimethylsiloxanes (PDMSs), polydiarylsiloxanes, polyalkylarylsiloxanes, silicone gums and resins, and also organopolysiloxanes (or organomodified polysiloxanes, or alternatively organomodified silicones) which are polysiloxanes including in their structure one or more organofunctional groups, generally attached via a hydrocarbon-based group, and preferably chosen from aryl groups, amine groups, alkoxy groups and polyoxyethylene or polyoxypropylene groups.

The organomodified silicones may be polydiarylsiloxanes, especially polydiphenylsiloxanes, and polyalkylarylsiloxanes, functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes including:
polyoxyethylene and/or polyoxypropylene groups optionally including $C_6$-$C_{24}$ alkyl groups, such as dimethicone copolyols, and especially those sold by the company Dow Corning under the name DC 1248 or the oils Silwet® L 722, L 7500, L 77 and L 711 from the company Union Carbide; or alternatively $(C_{12})$alkylmethicone copolyols, and especially those sold by the company Dow Corning under the name Q2-5200;
substituted or unsubstituted amine groups, in particular $C_1$-$C_4$ aminoalkyl groups; mention may be made of the products sold under the names GP4 Silicone Fluid and GP7100 by the company Genesee, or under the names Q2-8220 and DC929 or DC939 by the company Dow Corning;
thiol groups, such as the products sold under the names GP 72 A and GP 71 from Genesee;
alkoxylated groups, such as the product sold under the name Silicone Copolymer F-755 by SWS Silicones and Abil Wax® 2428, 2434 and 2440 by the company Goldschmidt;
hydroxylated groups, for instance polyorganosiloxanes containing a hydroxyalkyl function;
acyloxyalkyl groups, such as the polyorganosiloxanes described in patent USA-4957732;
anionic groups of the carboxylic acid type, as described, for example, in EP 186 507, or of the alkylcarboxylic type, such as the product X-22-3701E from Shin-Etsu; or alternatively of the 2-hydroxyalkylsulfonate or 2-hydroxyalkylthiosulfate type, such as the products sold by Goldschmidt under the names Abil® S201 and Abil® S255;
hydroxyacylamino groups, such as the polyorganosiloxanes described in patent application EP 342834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups.

Among these polydialkylsiloxanes, mention may be made of the following commercial products:
- the Silbione® oils of the 47 and 70047 series or the Mirasil® oils sold by Rhodia, for instance the oil 70047 V 500000;
- the oils of the Mirasil® series sold by the company Rhodia;
- the oils of the 200 series from Dow Corning, such as DC200, with a viscosity of 60000 mm²/s;
- the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Products that may be used more particularly in accordance with the invention are mixtures such as:
- mixtures formed from a polydimethylsiloxane hydroxylated at the chain end, or dimethiconol (CTFA), and from a cyclic polydimethylsiloxane, also known as cyclomethicone (CTFA), such as the product Q2-1401 sold by Dow Corning.

The polyalkylarylsiloxanes are chosen particularly from linear and/or branched polydimethyl/methylphenylsiloxanes and polydimethyl/diphenylsiloxanes with a viscosity ranging from $1\times10^{-5}$ to $5\times10^{-2}$ m²/s at 25° C.

Among these polyalkylarylsiloxanes, mention may be made of the products sold under the following names:
- the Silbione® oils of the 70641 series from Rhodia;
- the oils of the Rhodorsil® 70633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

The dye composition according to the invention may comprise one or more silicones in a total amount ranging from 0.01% to 30% by weight, preferably from 0.1% to 10% by weight and better still from 0.2% to 5% by weight, relative to the total weight of the dye composition.

Presentation Form

The dye composition according to the invention may especially be in the form of a suspension, a dispersion, a gel, an emulsion, especially an oil-in-water (O/W) or water-in-oil (W/O) emulsion, or a multiple (W/O/W or polyol/O/W or O/W/O) emulsion, in the form of a cream, a mousse, a stick, a dispersion of vesicles, especially of ionic or nonionic lipids, or a two-phase or multi-phase lotion. Preferably, the dye composition is in the form of a gel.

A person skilled in the art may select the appropriate presentation form, and also the method for preparing it, on the basis of his general knowledge, taking into account firstly the nature of the constituents used, especially their solubility in the support, and secondly the intended application of the composition.

The method according to the invention comprises a step of applying a makeup-removing composition to dyed keratin fibers such as the hair. This step may take place following the dyeing of the keratin fibers by the dye composition according to the invention after the optional step of applying heat to the keratin fibers, or after a defined time, i.e. days or weeks, after the application of the dye composition to the keratin fibers and the optional step of applying heat to the keratin fibers.

Makeup-Removing Composition

The makeup-removing composition may be in the form of an emulsion, a microemulsion, a two-phase composition or an anhydrous composition.

The term "anhydrous composition" means a composition which contains less than 2% by weight of water, or even less than 0.5% of water relative to the total weight of the composition, or in particular a composition free of water, the water not being added during the preparation of the composition but corresponding to the residual water provided by the mixed ingredients.

When the composition according to the invention is an emulsion, a microemulsion or a two-phase composition, it comprises an aqueous phase and an oily phase. The emulsions or microemulsions, on the one hand, and the two-phase compositions on the other hand, according to the invention are distinguished by the fact that the two-phase compositions are constituted of two phases which, at rest, are visibly distinct from one another other instead of being emulsified in one another.

When the composition is in the form of an emulsion, it may be a water-in-oil (W/O) or oil-in-water (O/W) emulsion, or a multiple (W/O/W or O/W/O) emulsion.

"Microemulsion" denotes a thermodynamically stable isotropic single liquid phase containing a ternary system having three components comprising an oily component, an aqueous component and a surfactant. In the present context, the term "microemulsion" denotes a "microemulsion in the narrow sense", i.e. a thermodynamically stable isotropic single liquid phase.

The microemulsion may be of O/W (oil-in-water) type in which the oil is solubilized by micelles, a microemulsion of W/O (water-in-oil) type in which the water is solubilized by reverse micelles, or a bicontinuous microemulsion in which the number of associations of surfactant molecules tends to infinity such that the aqueous phase and the oily phase both have a continuous structure.

The microemulsion may have a dispersed phase with a number-average diameter of 100 nm or less, preferably 50 nm or less and more preferably 20 nm or less, measured by laser particle size analysis.

Preferably, the makeup-removing composition according to the invention is in the form of a water-in-oil emulsion or a water-in-oil microemulsion.

More preferentially, the makeup-removing composition according to the invention is in the form of a water-in-oil microemulsion.

Oily Phase

Preferably, the makeup-removing composition comprises an oily phase.

The content of oily phase in the makeup-removing composition varies according to the formulation of the makeup composition (emulsion, microemulsion, anhydrous, etc.).

The oily phase comprises at least one hydrocarbon oil and may further comprise one or more fatty substances other than the hydrocarbon oils as described below.

Hydrocarbon Oil

The makeup-removing composition according to the invention comprises at least one hydrocarbon oil. Preferably, the oily phase of the makeup-removing composition comprises at least one hydrocarbon oil.

The term "oil" means a fatty substance that is liquid at room temperature (25° C.) and at atmospheric pressure (760 mmHg or $1.013 \times 10^5$ Pa).

The term "fatty substance" means an organic compound that is insoluble in water at ordinary temperature (25° C.) and at atmospheric pressure (760 mmHg or $1.013 \times 10^5$ Pa) (solubility of less than 5%, preferably of less than 1% and even more preferentially of less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The term "hydrocarbon oil" means an oil formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

Mention may be made of volatile hydrocarbon oils and non-volatile hydrocarbon oils. Preferably, the makeup-removing composition comprises at least one non-volatile hydrocarbon oil.

The term "non-volatile oil" means an oil that remains on the skin or the keratin fiber at room temperature and atmospheric pressure. More precisely, a non-volatile oil has an evaporation rate strictly less than 0.01 mg/cm²/min.

To measure this evaporation rate, 15 g of oil or of oil mixture to be tested are placed in a crystallizing dish 7 cm in diameter, which is placed on a balance in a large chamber of about 0.3 m³ that is temperature regulated, at a temperature of 25° C., and hygrometry regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed toward the crystallizing dish, 20 cm away from the bottom of the crystallizing dish. The mass of oil remaining in the crystallizing dish is measured at regular intervals. The evaporation rates are expressed in mg of oil evaporated per unit of area (cm²) and per unit of time (minutes).

The non-volatile hydrocarbon oils that are suitable for the present invention may be chosen in particular from:

hydrocarbon oils of plant origin, such as triglycerides constituted of fatty acid esters of glycerol, the fatty acids of which may have chain lengths ranging from $C_4$ to $C_{28}$, these fatty acids possibly being linear or branched, and saturated or unsaturated; these oils are in particular wheatgerm oil, sunflower oil, beauty-leaf oil, grapeseed oil, corn oil, apricot oil, castor oil, shea oil, avocado oil, olive oil, soybean oil, sweet almond oil, rapeseed oil, cottonseed oil, hazelnut oil, macadamia oil, jojoba oil, palm oil, alfalfa oil, poppy oil, pumpkin oil, sesame oil, marrow oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by the company Stéarineries Dubois or those sold under the names Miglyol 810®, 812® and 818® by the company Sasol;

synthetic ethers having from 10 to 40 carbon atoms;

linear or branched hydrocarbons, of mineral or synthetic origin, such as petroleum jelly, polybutenes, polydecenes and squalane;

synthetic esters and/or ethers such as the oils of formula $R_1COOR_2$ and/or $R_1OR_2$ in which $R_1$ represents the residue of a linear or branched fatty acid comprising from 1 to 40 carbon atoms and $R_2$ represents a hydrocarbon chain, in particular a branched hydrocarbon chain containing from 1 to 40 carbon atoms, on condition that the total number of carbons of $R_1+R_2$ is $>10$, such as for example purcellin oil (cetostearyl octanoate), isopropyl myristate, isopropyl palmitate, butyl stearate, $C_{12}$ to $C_{15}$ alkyl benzoate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, 2-diethylhexyl succinate, isostearyl isostearate, octanoates, decanoates or ricinoleates of alcohols or of polyalcohols, such as propylene glycol dioctanoate; hydroxylated esters such as isostearyl lactate and diisostearyl malate; lanolic acid, oleic acid, lauric acid or stearic acid esters; glyceryl or diglyceryl triisostearate; and pentaerythritol esters;

fatty alcohols that are liquid at room temperature, containing a branched and/or unsaturated carbon chain having from 12 to 26 carbon atoms, for instance cetanol, octyldodecanol, stearyl alcohol, linoleyl alcohol, linolenyl alcohol, isostearyl alcohol, oleyl alcohol, 2-hexyldecanol, 2-butyloctanol or 2-undecylpentadecanol;

fatty acids such as myristic acid, palmitic acid, stearic acid, behenic acid, oleic acid, linoleic acid, linolenic acid and isostearic acid; and mixtures thereof.

Preferably, the makeup-removing composition according to the invention comprises a total content of non-volatile hydrocarbon oil(s) ranging from 10% to 95% by weight, preferably from 20% to 80% by weight, and preferentially from 30% to 70% by weight, relative to the total weight of the makeup-removing composition.

The term "volatile oil" means an oil that can evaporate on contact with the skin in less than one hour, at room temperature and atmospheric pressure. The volatile oil is a cosmetic volatile oil, which is liquid at room temperature. More specifically, a volatile oil has an evaporation rate of between 0.01 and 200 mg/cm²/min, limits included (see protocol for measuring the evaporation rate above).

The volatile hydrocarbon oils suitable for the invention may be chosen from hydrocarbon oils having from 7 to 16 carbon atoms. The volatile hydrocarbon oils may be chosen from branched alkanes and linear alkanes.

Volatile hydrocarbon oils having from 7 to 16 carbon atoms that may especially be mentioned include branched $C_8$-$C_{16}$ alkanes, for instance $C_8$-$C_{16}$ isoalkanes (also known as isoparaffins), isododecane, isodecane, isohexadecane and, for example, the oils sold under the trade name Isopar or Permethyl, branched $C_8$-$C_{16}$ esters, for instance isohexyl neopentanoate, and mixtures thereof. Preferably, the volatile hydrocarbon oil having from 7 to 16 carbon atoms is chosen from isododecane, isodecane and isohexadecane, and mixtures thereof, and is especially isododecane.

As volatile hydrocarbon oils that may be used for the purposes of the present invention, mention may be made of linear alkanes, preferably of plant origin, comprising from 7 to 15 carbon atoms, in particular from 9 to 14 carbon atoms and more particularly from 11 to 13 carbon atoms.

As examples of linear alkanes that are suitable for the invention, mention may be made of n-heptane (C7), n-octane (C8), n-nonane (C9), n-decane (C10), n-undecane (C11), n-dodecane (C12), n-tridecane (C13), n-tetradecane (C14) and n-pentadecane (C15), and mixtures thereof, and in particular the mixture of n-undecane (C11) and n-tridecane (C13) described in Example 1 of patent application WO 2008/155059 by the company Cognis. Mention may also be made of n-dodecane (C12) and n-tetradecane (C14) sold by Sasol under the references, respectively, Parafol 12-97 and Parafol 14-97, and also mixtures thereof.

In this case, the makeup-removing composition according to the invention comprises a total content of volatile hydrocarbon oil(s) ranging from 0.1% to 10% by weight and better still from 0.5% to 5% by weight, relative to the total weight of the makeup-removing composition.

The hydrocarbon oil(s) according to the invention may also be defined according to their molecular weight and their solubility parameter δa.

Preferably, a hydrocarbon oil according to the invention has a molecular weight of less than or equal to 400 g/mol and a solubility parameter δa ranging from 2 to 15 $J^{0.5}/cm^{1.5}$.

The definition and calculation of the solubility parameters in the Hansen three-dimensional solubility space are described in the article by C. M. Hansen: "The three-dimensional solubility parameters", J. Paint Technol. 39, 105 (1967).

According to this Hansen space:
  δd characterizes the London dispersion forces derived from the formation of dipoles induced during molecular impacts;
  δp characterizes the Debye interaction forces between permanent dipoles and also the Keesom interaction forces between induced dipoles and permanent dipoles;
  δh characterizes the specific interaction forces (such as hydrogen bonds, acid/base, donor/acceptor, etc.);
  δa is determined by the equation $δa=(δp^2+δh^2)^{1/2}$ The parameters δd, δp, δh and δa are expressed in $(J/cm^3)^{1/2}$.

The total solubility parameter δ according to the Hansen solubility space is defined in the article "Solubility parameter values" by Eric A. Grulke in the book "Polymer Handbook", 3rd Edition, Chapter VII, pages 519-559, by the relationship:

$$δ=(δd^2+δp^2+δh^2)^{1/2}$$

Among the hydrocarbon oils having a molecular weight of less than or equal to 400 g/mol and a solubility parameter δa ranging from 2 to 15 $J^{0.5}/cm^{1.5}$, mention may be made of dicaprylyl ether (δa=3.45 $J^{0.5}/cm^{1.5}$), 2-ethylhexyl palmitate (δa=4.2 $J^{0.5}/cm^{1.5}$), cetyl 2-ethylhexanoate (δa=4.2 $J^{0.5}/cm^{1.5}$), octyldodecyl neopentanoate (δa=4.2 $J^{0.5}/cm^{1.5}$), isostearyl neopentanoate (δa=4.3 $J^{0.5}/cm^{1.5}$), isostearyl benzoate (δa=4.4 $J^{0.5}/cm^{1.5}$), tridecyl isononanoate (δa=4.4 $J^{0.5}/cm^{1.5}$), isopropyl stearate (δa=4.5 $J^{0.5}/cm^{1.5}$), isopropyl isostearate (δa=4.5 $J^{0.5}/cm^{1.5}$), isopropyl palmitate (δa=4.7 $J^{0.5}/cm^{1.5}$), isononyl isononanoate (δa=4.87 $J^{0.5}/cm^{1.5}$), C12-15 alkyl benzoate (δa=4.9 $J^{0.5}/cm^{1.5}$), isopropyl myristate (δa=5.0 $J^{0.5}/cm^{1.5}$), 2-ethylhexyl 2-ethylhexanoate (δa=5.2 $J^{0.5}/cm^{1.5}$), isodecyl neopentanoate (δa=5.3 $J^{0.5}/cm^{1.5}$), 2-ethylhexyl benzoate (δa=5.9 $J^{0.5}/cm^{1.5}$), caprylyl carbonate (δa=6.0 $J^{0.5}/cm^{1.5}$) sold under the name Cetiol CC by Cognis, dioctyl (2-ethylhexyl) carbonate (δa=6.0 $J^{0.5}/cm^{1.5}$), diethylhexyl adipate (δa=6.2 $J^{0.5}/cm^{1.5}$), octadecyl 5-oxo-L-prolinate (δa=6.2 $J^{0.5}/cm^{1.5}$), propylene glycol dipelargonate (δa=6.4 $J^{0.5}/cm^{1.5}$), neopentyl glycol dicaprate (δa=6.4 $J^{0.5}/cm^{1.5}$), dicaprylyl maleate (δa=6.6 $J^{0.5}/cm^{1.5}$), propylene glycol dioctanoate (δa=6.7 $J^{0.5}/cm^{1.5}$), dodecyl 1-butyl-5-oxopyrrolidine-3-carboxylate (δa=7.1 $J^{0.5}/cm^{1.5}$), 2,4-methyl-1,5-pentanediol dineopentanoate (δa=7.3 $J^{0.5}/cm^{1.5}$), 2-octyldodecanol (δa=7.7 $J^{0.5}/cm^{1.5}$), isostearyl alcohol (δa=8.1 $J^{0.5}/cm^{1.5}$), oleyl alcohol (δa=8.2 $J^{0.5}/cm^{1.5}$), diisopropyl adipate (δa=8.31 $J^{0.5}/cm^{1.5}$), diisobutyl adipate (δa=8.31 $J^{0.5}/cm^{1.5}$), hexyldecanol (δa=8.6 $J^{0.5}/cm^{1.5}$), propan-2-yl 1-(2-ethylhexyl)-5-oxopyrrolidine-3-carboxylate (δa=8.6 $J^{05}/cm^{1}$-5), propylene glycol monoisostearate (δa=8.7 $J^{05}/cm^{1.5}$), isostearyl lactate (δa=8.7 $J^{0.5}/cm^{1.5}$), butyl 1-butyl-5-oxopyrrolidine-3-carboxylate (δa=9.4 $J^{0.5}/cm^{15}$), 2-butyloctanol (δa=9.8 $J^{0.5}/cm^{1.5}$), C12-C13 alkyl lactate (δa=10.1 $J^{0.5}/cm^{1.5}$), dimethyl isosorbide (δa=10.76 $J^{0.5}/cm^{1.5}$), tributyl citrate (δa=11.41 $J^{0.5}/cm^{1.5}$), triethyl citrate (δa 5=13.7 $J^{05}/cm^{1}$-5), phenylethyl alcohol (δa=14.0 $J^{0.5}/cm^{1.5}$), PEG-8 (polyethylene glycol containing 8 ethylene glycol units) (δa=14.8 $J^{0.5}/cm^{1.5}$), and mixtures thereof.

According to one preferred embodiment, the makeup-removing composition comprises at least one hydrocarbon oil having a molecular weight of less than or equal to 400 g/mol and a solubility parameter $δ_a$ ranging from 2 to 15 $J^{0.5}/cm^{1.5}$, said oil being chosen preferably from synthetic ethers and esters, and preferably from isopropyl myristate ($δ_a$=5.0 $J^{0.5}/cm^{1.5}$), dicaprylyl ether ($δ_a$=3.45 $J^{0.5}/cm^{15}$), isononyl isononanoate ($δ_a$=4.87 $J^{0.5}/cm^{1.5}$), isodecyl neopentanoate ($δ_a$=5.3 $J^{0.5}/cm^{1.5}$), diisobutyl adipate ($δ_a$=8.31 $J^{0.5}/cm^{15}$), diisopropyl adipate ($δ_a$=8.31 $J^{0.5}/cm^{15}$), dimethyl isosorbide ($δ_a$=10.76 $J^{0.5}/cm^{1.5}$), tributyl citrate ($δ_a$=11.41 $J^{0.5}/cm^{15}$), and mixtures thereof.

Preferably, the makeup-removing composition comprises at least one hydrocarbon oil chosen from synthetic esters of formula $R_1COOR_2$ in which $R_1$ represents the residue of a fatty acid comprising from 8 to 29 carbon atoms and $R_2$ represents a branched or unbranched hydrocarbon chain, containing from 3 to 30 carbon atoms, and mixtures thereof.

More preferentially, the hydrocarbon oil(s) are chosen from isopropyl myristate, isononyl isononanoate, and mixtures thereof.

Preferably, the hydrocarbon oil(s) is (are) present in a total content ranging from 10% to 95% by weight, preferably from 20% to 80% by weight, and more preferentially from 30% to 70% by weight, relative to the total weight of the makeup-removing composition.

The oily phase is present in a content of between 0.1% and 80% by weight, preferably between 1% and 70% by weight, relative to the total weight of the makeup-removing composition.

Aqueous Phase

Preferably, the makeup-removing composition comprises an aqueous phase.

The aqueous phase comprises water. It may also comprise at least one water-soluble organic solvent.

The term "water-soluble organic solvent" means an organic solvent that is miscible with water at 25° C.

Among the water-soluble organic solvents that may be used in the makeup-removing composition, mention may be made especially of monoalcohols having from 1 to 5 carbon atoms such as ethanol, isopropanol and butanol, and glycols having from 2 to 8 carbon atoms such as ethylene glycol, propylene glycol, 1,3-butylene glycol and dipropylene glycol.

Preferably, the aqueous phase (water and optionally the water-miscible solvent) is then present in the makeup-removing composition in a content ranging from 0.5% to 30% by weight, relative to the total weight of the makeup-removing composition, more preferentially ranging from 1% to 20% by weight, and better still from 5% to 15% by weight, relative to the total weight of the makeup-removing composition.

When the makeup-removing composition according to the invention comprises water, the water content preferably varies from 0.5% to 30% by weight, preferentially from 1% to 20% by weight and better still from 2% to 10% by weight, relative to the total weight of the makeup-removing composition.

Surfactants

The makeup-removing composition may comprise one or more surfactants.

The surfactant may be chosen from nonionic surfactants, anionic surfactants, amphoteric or zwitterionic surfactants, and mixtures thereof.

Mention may be made, as surfactants that can be used in the makeup-removing composition according to the invention:

among the nonionic surfactants, of:
glycerol ethers which are preferably oxyalkylenated, oxyethylenated and/or oxypropylenated, which may comprise from 10 to 150 oxyethylene and/or oxypropylene units;
oxyalkylenated alcohols, in particular oxyethylenated and/or oxypropylenated alcohols, which may comprise from 2 to 150 oxyethylene and/or oxypropylene units, preferably from 5 to 100 oxyethylene units, in particular ethoxylated $C_8$-$C_{24}$ and preferably $C_{12}$-$C_{18}$ fatty alcohols such as ethoxylated stearyl alcohol comprising 20 oxyethylene units (CTFA name: Steareth-20) such as Brij 78 sold by the company Uniqema, or ethoxylated cetearyl alcohol comprising 30 oxyethylene units (CTFA name: Ceteareth-30) and the mixture of $C_{12}$-$C_{15}$ fatty alcohols comprising 7 oxyethylene units (CTFA name: C12-15 Pareth-7), for instance the product sold under the name Neodol 25-7® by Shell Chemicals;
esters of a fatty acid, especially a $C_8$-$C_{24}$ and preferably $C_{16}$-$C_{22}$ fatty acid, and of polyethylene glycol (or PEG) (which may comprise from 10 to 150 oxyethylene units), such as PEG-50 stearate and PEG-40 monostearate sold under the name Myrj 52P® by the company Uniqema;
esters of a fatty acid, especially a $C_8$-$C_{24}$ and preferably $C_{16}$-$C_{22}$ fatty acid, and of glycerol ethers which are preferably oxyalkylenated, oxyethylenated and/or oxypropylenated (which may comprise from 10 to 150 oxyethylene and/or oxypropylene units), for instance polyoxyethylenated glyceryl monostearate comprising 200 oxyethylene units, sold under the name Simulsol 220 TM® by the company SEPPIC; polyoxyethylenated glyceryl stearate comprising 30 oxyethylene units, for instance the product Tagat S® sold by the company Goldschmidt, polyoxyethylenated glyceryl oleate comprising 30 oxyethylene units, for instance the product Tagat O® sold by the company Goldschmidt, polyoxyethylenated glyceryl cocoate comprising 30 oxyethylene units, for instance the product Varionic LI 13® sold by the company Sherex, polyoxyethylenated glyceryl isostearate comprising 30 oxyethylene units, for instance the product Tagat L® sold by the company Goldschmidt, and polyoxyethylenated glyceryl laurate comprising 30 oxyethylene units, for instance the product Tagat I® from the company Goldschmidt;
esters of a fatty acid, especially a $C_8$-$C_{24}$ and preferably $C_{16}$-$C_{22}$ fatty acid, and of sorbitol ethers which are preferably oxyalkylenated, oxyethylenated and/or oxypropylenated (which may comprise from 2 to 150 oxyethylene and/or oxypropylene units), for instance the polysorbate 60 sold under the name Tween 60® by the company Uniqema or the polysorbate 21 old under the name Tween 21-LQ® by the company Croda;
and mixture(s) thereof.

among the anionic surfactants, of:
alkyl phosphates;
alkyl sulfates, and in particular alkyl ether sulfates, alkylamido ether sulfates, alkylaryl polyether sulfates and monoglyceride sulfates;
alkyl sulfonates, alkylamide sulfonates, alkylaryl sulfonates, α-olefin sulfonates, paraffin sulfonates;
alkyl sulfosuccinates, alkyl ether sulfosuccinates and alkylamide sulfosuccinates;
alkyl sulfosuccinamates;
alkyl sulfoacetates;
acyl sarcosinates, acyl glutamates, acyl isethionates, N-acyl taurates and acyl lactylates;
alkylpolyglycoside carboxylic esters, such as alkylglucoside citrates, alkylpolyglycoside tartrates, alkylpolyglycoside sulfosuccinates or alkylpolyglycoside sulfosuccinamates; and
fatty acids, and salts thereof, in particular oleic acid, ricinoleic acid, palmitic acid or stearic acid salts, coconut oil or hydrogenated coconut oil acids;
alkyl-D-galactoside uronic acids and salts thereof, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and salts thereof, in particular those containing from 2 to 50 alkylene oxide and in particular ethylene oxide groups;
and mixtures thereof; preferably from fatty acid salts.

among amphoteric or zwitterionic surfactants, of:
alkylamphoacetates such as N-disodium N-cocoyl-N-carboxymethoxyethyl-N-carboxymethylethylenediamine (CTFA name: Disodium cocoamphodiacetate) sold as an aqueous saline solution under the name Miranol C2M Conc NP by the company Rhodia Chimie; N-sodium N-cocoyl-N-hydroxyethyl-N-carboxymethylethylenediamine (CTFA name: sodium cocamphoacetate); cocamides, for instance the mixture of coconut acid ethanolamides (CTFA name: Cocamide DEA).

Preferably, the surfactant(s) are chosen from nonionic surfactants.

Preferably, the nonionic surfactant(s) are chosen from esters of a $C_8$-$C_{24}$ and preferably $C_{16}$-$C_{22}$ fatty acid, and of sorbitol ethers which are preferably oxyalkylenated, oxyethylenated and/or oxypropylenated.

Preferably, the makeup-removing composition comprises at least one nonionic surfactant chosen from esters of a fatty acid, especially a $C_8$-$C_{24}$ and preferably $C_{16}$-$C_{22}$ fatty acid, and of preferably oxyalkylenated, oxyethylenated and/or oxypropylenated sorbitol ethers.

Preferably, when the makeup-removing composition comprises one or more surfactants, the total amount of surfactant(s) ranges from 1% to 50% by weight, more preferentially from 5% to 45% by weight and better still from 10% to 35% by weight, relative to the total weight of the makeup-removing composition.

Additives

The makeup-removing composition may also contain any adjuvant or additive usually used.

Among the additives that may be contained in the makeup-removing composition, mention may be made in particular of preservatives, antioxidants, fragrances, mattifying fillers, cosmetic active agents, thickeners, lipophilic or hydrophilic polymers and sequestrants.

Method for Dyeing and Removing Makeup from and/or Cleansing Keratin Fibers

The present invention relates to a method for treating human keratin fibers such as the hair comprising a step of applying to the keratin fibers a dye composition as described above, optionally a step of applying heat to the dyed keratin fibers using a heating tool and a step of applying, to the dyed keratin fibers, a makeup-removing composition as defined above.

The application of the dye composition to the keratin fibers is carried out before the optional step of applying heat to the keratin fibers and before the application of the makeup-removing composition.

The dye composition according to the invention may be used on wet or dry keratin fibers, and also on any type of fair or dark, natural or dyed, permanent-waved, bleached or straightened fibers.

According to a particular embodiment of the method of the invention, the fibers are washed before application of the dye composition described above.

The application of the dye composition to the keratin fibers may be carried out by any conventional means, in particular using a comb, a fine brush, a coarse brush or with the fingers.

The dyeing method, i.e. application of the dye composition to the keratin fibers, is generally carried out at room temperature (between 15 and 25° C.).

The method according to the invention may comprise a step of applying heat to the dyed keratin fibers using a heating tool.

When the method of the invention implements a step of applying heat to the keratin fibers, the step of applying heat to the keratin fibers takes place after the application of the dye composition to the keratin fibers.

The step of applying heat to the keratin fibers may be performed after the application of the dye composition and before the application of the makeup-removing composition to the keratin fibers.

Preferably, the step of applying heat to the keratin fibers using a heating tool is carried out at a temperature ranging from 30° C. to 250° C., preferably from 50° C. to 230° C., more preferentially from 60° C. to 220° C. and better still from 100° C. to 210° C.

The heat application step of the method of the invention may be carried out using a hood, a hairdryer, a straightening iron, a curling iron, a Climazone, etc.

Preferably, the heat application step of the method of the invention is carried out using a hairdryer and/or a straightening iron, more preferentially using a straightening iron.

During the step of applying heat to the keratin fibers, a mechanical action may be exerted on the locks, such as combing, brushing or running the fingers through.

When the step of applying heat to the keratin fibers is carried out using a hood or a hairdryer, the temperature is preferably between 30° C. and 110° C., preferentially between 50° C. and 90° C.

When the step of applying heat to the keratin fibers is carried out using a straightening iron, the temperature is preferably between 110° C. and 220° C., preferably between 140° C. and 200° C.

In a particular variant, the method of the invention implements a step (b1) of applying heat using a hood, a hairdryer or a Climazone, preferably a hairdryer and a step (b2) of applying heat using a straightening or curling iron, preferably a straightening iron.

Step (b1) may be performed before step (b2).

During step (b1), also referred to as the drying step, the fibers may be dried, for example at a temperature above or equal to 30° C. According to a particular embodiment, this temperature is above 40° C. According to a particular embodiment, this temperature is above 45° C. and below 110° C.

Preferably, if the fibers are dried, they are dried, in addition to a supply of heat, with a flow of air. This flow of air during drying makes it possible to improve the strand separation of the coating.

During drying, a mechanical action may be exerted on the locks, such as combing, brushing or running the fingers through.

During step (b2), the passage of the straightening or curling iron, preferably straightening iron, may be carried out at a temperature ranging from 110° C. to 220° C., preferably between 140° C. and 200° C.

The makeup-removing composition is applied to keratin fibers dyed with the dye composition as defined above and after the step of applying heat to the dyed keratin fibers when the method implements a step of applying heat to the dyed keratin fibers.

The application of the makeup-removing composition can be carried out on dry dyed keratin fibers or wet dyed keratin fibers and also on all types of fibers.

The makeup-removing method is generally carried out at room temperature (between 15° C. and 25° C.).

The application of the makeup-removing composition may be carried out immediately after the application of the dye composition once the optional application of heat to the hair has been carried out (i.e. a few minutes to a few hours after the application of the dye composition), or in the days or weeks following the application of the dye composition and the optional step of applying heat to the hair.

The makeup-removing composition may be applied with the aid of any suitable support, which is especially capable of absorbing it, for example a fibrous makeup-removing disk, for example a woven or nonwoven fabric, cotton wool, a flocked film, a sponge, a wipe, or a twisted or injection-molded mascara application brush.

The makeup-removing composition may be contained in a container and taken up gradually each time makeup is removed. As a variant, the makeup-removing composition impregnates the support used for removing makeup, the support possibly being packaged, in this case, for example in leaktight packaging.

After the makeup-removing composition has been used, the keratin fibers may not be rinsed. As a variant, they may be rinsed. The rinsing may be performed, for example, with running water, without addition of a soap.

The present invention will now be described more specifically by means of examples, which do not in any way limit the scope of the invention. However, the examples make it possible to support specific characteristics, variants and preferred embodiments of the invention.

EXAMPLE

Example 1

Dye Composition
Compositions (g/100 g)

| Composition | A (invention) |
|---|---|
| Isobutyl methacrylate/bis-hydroxypropyl dimethicone acrylate copolymer (containing 40% active material in isododecane)[1] | 25 |
| Pigment rouge | 6 |
| isododecane | qs 100 |

[1] sold under the trade name Granacrysil BMAS by Grant Industries

Protocol:

The dye composition A is applied to locks of natural hair containing 90% white hairs in a proportion of 0.5 g of composition per gram of lock.

The locks of hair are then combed and dried with a hairdryer.

A straightening iron is then passed over each of the locks five times at a temperature of 190° C.

The hair is dyed uniformly and intensely.

The hair thus dyed is then subjected to a test of several repeated shampoo washes so as to evaluate the persistence (resistance) of the coloring obtained with respect to shampoo washes.

Shampoo Wash Protocol:

The locks are washed with standard shampoo respectively at T=0 (i.e. immediately after the application of the dye composition to the keratin fibers and after the application of the straightening iron to the locks of hair).

The locks of hair are then rinsed, combed and dried with a hairdryer.

Lastly, a straightening iron is then passed over each of the locks five times at a temperature of 190° C.

The next shampoo wash is then performed on the locks obtained after the passes of the straightening iron.

Results:

The resistance of the color of the locks was evaluated in the CIE L*a*b* system, using a Minolta Spectrophotometer CM3600D colorimeter.

In this L*a*b* system, L* represents the intensity of the color, a* indicates the green/red color axis and b* the blue/yellow color axis.

The resistance of the coloring is evaluated by the color difference ΔE between the dyed locks before shampooing, then after having undergone 3 and 10 shampoo washes according to the protocol described above. The lower the value of ΔE, the more shampoo-resistant the color.

| Number of shampoo washes | L* | a* | b* | ΔE |
|---|---|---|---|---|
| 0 | 35 | 37 | 17 | |
| 3 | 35 | 37 | 15 | 2.0 |
| 10 | 39 | 32 | 10 | 9.5 |

The hair has a natural feel and the strands of hair may be separated with the fingers or by using a comb and/or a brush.

The locks of hair dyed with the dye composition A and washed with three or ten shampoo washes have low values of ΔE.

Thus, the hair is dyed and the colored coating of the keratin fibers is shampoo-resistant. Specifically, the locks of hair washed with three or ten shampoo washes have a good color resistance.

Makeup-Removing Composition
Compositions (g/100 g)

| Composition | B (invention) |
|---|---|
| Polysorbate 21 | 30 |
| Isopropyl myristate | 30 |
| Isononyl isononanoate | 30 |
| Ethanol | 3 |
| Caprylyl glycol | 0.5 |
| preservative | qs |
| water | qs 100 |

Protocol:

The locks of hair dyed by the dye composition A are treated with the makeup-removing composition B once the dyed locks are dry to the touch, in a proportion of 0.5 g of composition B per gram of lock.

The locks of hair dyed by the dye composition A are rinsed with the makeup-removing composition B three times in succession. Between each application of the makeup-removing composition, the locks are rinsed with water.

After the three applications of the makeup-removing composition, the locks are placed on absorbent paper and dried with a hairdryer.

Results:

As the number of washes with the makeup-removing composition increases, the hair is rapidly bleached.

Example 2

Dye Composition
Protocol:

The dye composition A of example 1 is applied to locks of natural hair containing 90% white hairs in a proportion of 0.5 g of composition per gram of lock.

The locks of hair are then combed and dried with a hairdryer.

A straightening iron is then passed over each of the locks five times at a temperature of 190° C.

The hair is dyed uniformly and intensely.

Makeup-Removing Composition
Compositions (g/100 g)

| Composition | C (comparative) |
|---|---|
| Polysorbate 21 | 90 |
| Ethanol | 3 |
| Caprylyl glycol | 0.5 |
| preservative | qs |
| water | qs 100 |

Protocol:

The locks of hair dyed by the dye composition A are treated with the makeup-removing composition B according to the invention (described in example 1) and with the makeup-removing comparative composition C once the dyed locks are dry to the touch, in a proportion of 0.5 g of composition per gram of lock.

The locks of hair dyed by the dye composition A are rinsed with the makeup-removing composition B according to the invention (as described in example 1) and with the makeup-removing comparative composition C three times in succession. Between each application of the makeup-removing composition, the locks are rinsed with water.

After the three applications of the makeup-removing composition, the locks are placed on absorbent paper and dried with a hairdryer.

Results:

The resistance of the color of the locks was evaluated in the CIE L*a*b* system, using a Konica Minolta CM-3600A colorimeter.

In this L*a*b* system, L* represents the intensity of the color, a* indicates the green/red color axis and b* the blue/yellow color axis.

The resistance of the coloring is evaluated by the color difference ΔE between the dyed locks before applying the makeup-removing composition, then applying the makeup-removing composition B according to the invention (as described in example 1) and with the makeup-removing comparative composition C, according to the protocol described above. The lower the value of ΔE, the more resistant is the color to the makeup-removing composition.

| Compositions | L* | a* | b* | ΔE |
|---|---|---|---|---|
| Composition A | 35.4 | 41.3 | 17.4 | |
| Composition A + C | 47.3 | 22.8 | 12.2 | 22.60 |
| Composition A + B | 63.1 | 6.4 | 17.3 | 44.56 |

The locks of hair dyed with the dye composition A and treated with the makeup-removing composition B according to the invention have higher value of ΔE than the locks of hair dyed with the dye composition A and treated with the makeup-removing comparative composition C.

Thus, the makeup-removing composition B according to the invention is more efficient for cleansing the hair than the comparative makeup-removing composition C.

The invention claimed is:

1. A method for treating human keratin fibers, comprising:
   a) applying to the keratin fibers a composition comprising:
      at least one silicone acrylic copolymer comprising:
         a polyalkylsiloxane unit, and
         at least one alkyl acrylate or methacrylate unit comprising an alkyl radical comprising from 1 to 30 carbon atoms; and
      at least one pigment;
   b) optionally applying heat to the keratin fibers using a heating tool; and
   c) applying to the keratin fibers a makeup-removing composition comprising at least one hydrocarbon oil.

2. The method of claim 1, wherein the at least one silicone acrylic copolymer comprises at least two alkyl acrylate or methacrylate units.

3. The method of claim 1, wherein the alkyl radical of the at least one alkyl acrylate or methacrylate unit comprises from 1 to 10 carbon atoms.

4. The method of claim 1, wherein the at least one silicone acrylic copolymer comprises:
   a polydimethylsiloxane (PDMS) unit, and
   an alkyl acrylate or methacrylate unit comprising an alkyl radical having from 1 to 30 carbon atoms.

5. The method of claim 1, wherein the at least one silicone acrylic copolymer comprises:
   a polydimethylsiloxane (PDMS) unit comprising at least one polymerizable radical group chosen from an acrylic or methacrylic group having from 1 to 6 carbon atoms; and
   a $C_1$-$C_{22}$ alkyl acrylate or methacrylate unit.

6. The method of claim 1, wherein the at least one silicone acrylic copolymer comprises:
   a polydimethylsiloxane (PDMS) unit comprising at least one polymerizable radical group chosen from a $CH_2{=}CH{-}CO{-}O{-}R_1{-}$ group, where $R_1$ represents an alkyl radical comprising from 1 to 3 carbon atoms; and
   a $C_1$-$C_{10}$ alkyl acrylate or methacrylate unit.

7. The method of claim 1, wherein the at least one silicone acrylic copolymer is present in a total amount ranging from 1% to 50% by weight, relative to the total weight of the composition.

8. The method of claim 1, wherein the at least one pigment is present in a total amount ranging from 0.01% to 30% by weight, relative to the total weight of the composition.

9. The method of claim 1, wherein the composition further comprises at least one oil.

10. The method of claim 9, wherein the at least one oil is present in a total amount ranging from 10% to 99% by weight, relative to the total weight of the composition.

11. The method of claim 1, wherein the makeup-removing composition comprises at least one non-volatile hydrocarbon oil.

12. The method of claim 1, wherein the at least one hydrocarbon oil is chosen from synthetic esters of formula:

$$R_1COOR_2,$$

wherein $R_1$ represents the residue of a fatty acid comprising from 8 to 29 carbon atoms, and $R_2$ represents a branched or unbranched hydrocarbon chain containing from 3 to 30 carbon atoms.

13. The method of claim 1, wherein the at least one hydrocarbon oil is chosen from isopropyl myristate, isononyl isononanoate, or mixtures thereof.

14. The method of claim 1, wherein the at least one hydrocarbon oil is present in a total amount ranging from 10% to 95% by weight, relative to the total weight of the makeup-removing composition.

15. The method of claim 1, wherein the makeup-removing composition further comprises at least one nonionic surfactant chosen from esters of $C_8$-$C_{24}$ fatty acids.

16. The method of claim 1, wherein the application of the composition to the keratin fibers is carried out before the optional application of heat to the keratin fibers and before the application of the makeup-removing composition to the keratin fibers.

17. The method of claim 1, wherein the application of heat to the keratin fibers is carried out before the application of the makeup-removing composition to the keratin fibers.

18. The method of claim 1, wherein applying heat to the keratin fibers using a heating tool having a temperature ranging from 30° C. to 250° C.

19. The method of claim 1, wherein applying heat to the keratin fibers is carried out using a straightening iron.

* * * * *